US012687536B1

(12) United States Patent
Guo et al.

(10) Patent No.: US 12,687,536 B1
(45) Date of Patent: Jul. 21, 2026

(54) DETERMINING ROCK FRAGMENT SIZE AND SIZE DISTRIBUTION

(71) Applicant: Halliburton Energy Services, Inc., Houston, TX (US)

(72) Inventors: Yonggui Guo, Houston, TX (US); Claudia Lucia Bonin De Oliveira, Houston, TX (US); Dale E. Jamison, Humble, TX (US); Mateusz Michal Dyngosz, Houston, TX (US); Mahdi Parak, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 19/035,669

(22) Filed: Jan. 23, 2025

(51) Int. Cl.
| | |
|---|---|
| *G01N 33/24* | (2006.01) |
| *E21B 44/00* | (2006.01) |
| *G01N 15/0205* | (2024.01) |

(52) U.S. Cl.
CPC ............. *G01N 33/24* (2013.01); *E21B 44/00* (2013.01); *G01N 15/0211* (2013.01)

(58) Field of Classification Search
CPC ..... G01N 33/24; G01N 15/0211; E21B 44/00
See application file for complete search history.

(56) References Cited

U.S. PATENT DOCUMENTS

2016/0138371 A1 * 5/2016 Loaiza .................... E21B 41/00
703/2

FOREIGN PATENT DOCUMENTS

| | | | | |
|---|---|---|---|---|
| CN | 116950652 A | * | 10/2023 | ........... E21B 49/005 |
| CN | 116952709 | | 10/2023 | |

OTHER PUBLICATIONS

Cai, et al., "Experimental Study on the Fractal Characteristics of Rocks Crushing", Matec Web Conf 2015, 2015, 6 pages.

Chien, et al., "Settling Velocity of Irregularly Shaped Particles", SPE Drilling & Completion, 1994, 281-289.

Kern, et al., "Techniques for Determining Size and Shape of Drill Cuttings", Brazilian Journal of Petroleum and Gas 16(2), 2022, 65-77.

Muto, et al., "Fractal Particle Size Distribution of Pulverized Fault Rocks as a Function of Distance From the Fault Core", Geophysical Research Letters, 42, 2015, 9 pages.

"PCT Application No. PCT/US25/59294 International Search Report and Written Opinion", Apr. 22, 2026, 9 pages.

Li, et al., "Fractal Behavior of Size Distribution and Specific Surface Area of Blasting Fragments", Applied Sciences, Oct. 29, 2023, vol. 13, No. 21, pp. 1-17; pp. 1, 4-14, Oct. 29, 2023, 17 pages.

Min, et al., "Fragmentation Fractal Analysis on Particle-size Distribution", Journal of the korean geotechnic al society. 2003, vol. 19, No. 2, 199-206. pp. 199-206; pp. 202-205, 2003, 8 pages.

(Continued)

*Primary Examiner* — Dany E Akakpo
(74) *Attorney, Agent, or Firm* — DeLizio, Peacock, Lewin & Guerra LLP

(57) ABSTRACT

Techniques for determining a rock fragment size and size distribution include determining rock fragment parameters associated with a well systems. The techniques further include determining a fractal dimension based, at least in part, on the rock fragment parameters. The techniques further include determining a rock fragment size distribution based, at least in part, on the fractal dimension.

23 Claims, 8 Drawing Sheets

(56)         References Cited

OTHER PUBLICATIONS

Xiao, et al., "Investigation on Coal Fragmentation by High-Velocity Water Jet in Drilling: Size Distribution s and Fractal Characteristics", Applied Sciences. Oct. 19, 2018, vol. 8, No. 10, pp. 1-20. pages 1-5, 8-9, 13, Oct. 19, 2018, 20 pages.
Yang, et al., "Fractal Characteristics of Drilling Particle Size Distribution of Shale: A Laboratory Scale Investigation", Rock Mechanics and Rock Engineering. Jun. 11, 2022, vol. 55, pp. 5307-5319. pages 5307-5310, 5318, Jun. 11, 2022, 13 pages.

* cited by examiner

400

700

START

Determine Default Value for
Maximum Caving Diameter — 702

Determine Default Value for
Fractal Dimension — 704

Determine Rock Fragment Size Distribution
Based on Default Maximum Caving
Diameter and Default Fractal Dimension — 706

Determine One or More Operational
Parameters Based on Size
Distribution — 708

Yes

Operational
Parameters
Change? — 710

No

END

DETERMINING ROCK FRAGMENT SIZE AND SIZE DISTRIBUTION

BACKGROUND

Well system drilling operations may result in the creation of rock fragments from the surrounding formation. These rock fragments may result in changes to various operational parameters, such as drilling fluid density and viscosity. Knowledge of the sizes and size distributions of the rock fragments can be used to improve the drilling operations.

BRIEF DESCRIPTION OF THE DRAWINGS

Embodiments of the disclosure may be better understood by referencing the accompanying drawings.

DESCRIPTION

Figure 1:
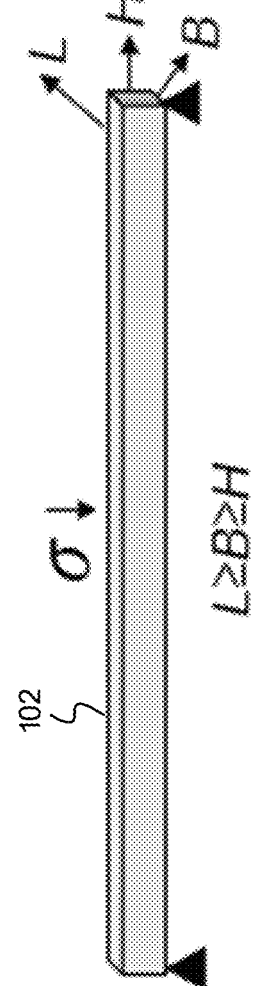
FIG. 1 depicts an example model of the bending of a caving induced by drilling fluid circulation, according to some implementations.

The description that follows includes example systems, methods, techniques, and program flows that embody aspects of the disclosure. However, it is understood that this disclosure may be practiced without these specific details. In some instances, well-known instruction instances, protocols, structures, and techniques have not been shown in detail in order not to obfuscate the description.

Well system operations, such as drilling, may use various techniques that employ magnetic fields for measurements. For example, a ranging tool may be lowered into a first well and made to generate a large magnetic field. The magnetic field generated by the ranging tool can be used to determine the distance between the first well and a second well. As another example, wireline applications, where instruments and tools are lowered down into the wellbore after drilling is completed, can benefit for similar reasons.

"Cuttings" and "cavings" are two forms of rock fragments that may be generated during drilling operations. "Cuttings" are rock fragments that are chipped away by the drill bit during the drilling operations, while "cavings" are rock fragments that break away from the wellbore wall because of insufficient mud weight. The addition of the rock fragments to the drilling fluid may cause the drilling fluid density and viscosity to change, which may result in changes to well system characteristics and operational parameters. Thus, determining the size and size distribution of the rock fragments may allow operators to adjust the operations to account for the rock fragments.

Similarly, predicting the size and size distribution of the rock fragments prior to beginning the drilling operations may allow the well system to be designed in a more optimal manner. For example, knowledge of the size and size distribution of the rock fragments can improve the prediction of the equivalent circulating density and improve solid transportation simulations, hydraulic simulation, and hole cleaning efficiency evaluation.

Fractal theory can be used to determine and predict the size and size distribution of rock fragments at the surface of the well system. In particular, the rock fragment size and size distribution are qualified with two parameters, $d_{max}$ and D, where $d_{max}$ is the maximum rock fragment size and D is the fractal dimension. As discussed in more detail below, the two parameters can be measured or estimated using different techniques. Further, techniques for determining the maximum size of cavings may take into account the caving shape (e.g., elongated or spherical/subspherical).

In addition to only using two parameters, the usage of fractal theory to determine rock fragment size and size distribution does not require continued measurement of the rock fragments if there are no changes in drilling parameters, bit properties, and formation properties. Further, it allows for the prediction of rock fragment size and size distribution even if the rock fragment size cannot be measured. Further, determining the maximum caving size can take into account the caving shape.

In some implementations, a system operation or attribute in the wellbore or other system component may be modified or updated based on the rock fragment size distribution. For example, an operation (at the surface, downhole, within a pipeline, etc.) may be performed and/or directed to be performed to change a downhole operation or attribute based on the particular rock fragment size distribution. For example, attributes of an actual drilling or extraction operation in the wellbore may be set based on the particular rock fragment size distribution. Examples of such attributes of the drilling/extraction operation may include drilling fluid/mud density, hydraulic pressure, etc. For further example, operations in a wellbore or other system component that may performed or modified in response to the determination of the size distribution of rock fragments may be changing the density of the drilling mud used.

For example, a rock fragment transportation simulation may be performed to evaluate hole cleaning efficiency based on the particular rock fragment size and size distribution. The evaluation may then be applied to optimize drilling parameters and drilling fluid properties, including but not limited to rate of penetration, rotations per minute, flow rate, drilling fluid density, and viscosity. A hydraulic simulation may be also performed to predict drilling fluid equivalent circulating density based on the particular rock fragment size and size distribution. The simulation allows engineers to prevent and mitigate potential drilling problems like stuck pipe, lost circulation, etc., by understanding the drilling fluid pressures acting on formations under different drilling conditions. For complex well trajectories, hydraulic simulations can help quantify the impact of directional drilling on fluid pressure, fluid flow and rock fragment transportation, allowing for better planning and mitigation of potential issues.

The size distribution of rock fragments can be described by the fractal size distribution using Equation 1, where M is the mass of the rock fragments per unit volume having a size smaller than d; $M_T$ is the total mass of rock fragments per unit volume; and $d_{max}$ is the maximum rock fragment size.

The power law size distribution can be quantified by determining the fractal dimension D.

$$\frac{M(\text{cutting size} < d)}{M_T} = \left(\frac{d}{d_{max}}\right)^{3-D} \qquad \text{Equation 1}$$

If the rock fragment is spherical, $d_{max}$ is the diameter of the rock fragment. If the rock fragment is not spherical, $d_{max}$ is the maximum dimension of the rock fragment.

An example technique for determining the size distribution involves performing a sieve analysis of rock fragment samples. In particular, a number of samples of rock fragments are collected during drilling operations. Sieves of varying sizes are used to divide the samples into size classes based on the size of the rock fragments. The mass of the rock fragments within each size class is then determined. Further, the total rock fragment mass is determined along with the cumulative mass of rock fragments smaller than a given cutting size (i.e., M(cutting size<d) in Equation 1).

Rewriting Equation 1 in linear form gives Equation 2:

$$\log\frac{M(\text{cutting size} < d)}{M_T} = (3 - D)\log\left(\frac{d}{d_{max}}\right) \qquad \text{Equation 2}$$

Equation 2 can be used to generate a linear graph by substituting the corresponding values for each size class from a single sample into the equation. The fractal dimension can be determined by solving for D and determining the average fractal dimension of all samples. Verification that the rock fragments correspond to a fractal distribution can be verified by analyzing the strength of the linear relationship within each sample (e.g., using a best-fit line and the corresponding correlation coefficients).

The fractal dimension and the maximum rock fragment size may not be constant values and, instead, may be affected by rock properties (e.g., rock strength and clay content) and bit type and drilling parameters (e.g., amount of weight on the bit, torque on the bit, and rotations per minute).

Once the fractal dimension and the maximum rock fragment size are determined, rock fragment size distribution can be determined. In particular, the rock fragment size $d_n$ for any given cumulative mass percentage n can be calculated using Equation 3:

$$d_n = d_{max}\left(\frac{n}{100}\right)^{\frac{1}{3-D}} (0 < n \leq 100) \qquad \text{Equation 3}$$

For example, rock fragment size $d_{50}$ represents a rock fragment size below which the cumulative mass of the rock fragments is 50% of the total mass of the rock fragments and can be determined by setting n in Equation 3 to 50.

Maximum Caving Size at the Surface

The maximum size of a caving that can be transported to the surface by drilling fluid is affected by its shape. In particular, the maximum size of an elongated caving (such as a platy caving) is limited by bending deformation encouraged by the special geometry, while the maximum size of a subspherical caving (such as a blocky caving) is dependent primarily on its slip velocity. Thus, different techniques can be used to determine the maximum size of cavings at the surface.

After a caving breaks off the wellbore wall and falls into the wellbore, it may continue breaking due to pipe rotation and drilling fluid circulation. There are many different active deformation mechanisms that can lead to continued caving fragmentation during caving transportation to surface, such as shearing, twisting, tensioning, and bending. Because bending is the most energy efficient deformation mechanism to break a caving, particularly for elongated cavings, the maximum possible size of an elongated caving at the surface is limited by bending deformation because of drilling fluid circulation. Thus, the maximum size of an elongated caving at the surface can be determined by assuming that the shape of the caving can be approximated by a rectangular prism and that the caving is deformed under a simply supported, uniformly distributed load.

FIG. 1 depicts an example model of the bending of a caving induced by drilling fluid circulation, according to some implementations. In particular, FIG. 1 depicts an example model 100 of the bending of a caving induced by drilling fluid circulation. The example model 100 comprises a rectangular prism 102 approximating the shape of a caving having side lengths L, H, and B, respectively. As noted above, the relationship between L, B, and H is defined by L≥B≥H. Thus, L defines the caving minimum size while L quantifies the caving maximum size. The caving is simply supported and bends under a uniformly distributed load σ.

The flow of drilling fluid within the wellbore exerts a force on the caving and may cause the caving to break. Given the caving shape (approximated by the rectangular prism 102), the caving is most likely to break by the force of the drilling fluid being exerted on the largest face of the caving (i.e., L). Thus, the maximum size of an elongated caving can be determined based, at least in part, on the properties of the example model 100 and its interaction with the drilling fluid within the wellbore. In particular, the maximum size of an elongated caving is the size at which the drilling fluid is unlikely to impart enough force onto the caving to cause the caving to bend to such a degree that it breaks.

The maximum bending stress of an elongated caving can be determined based, at least in part, on the caving maximum bending moment, the caving minimum centroid moment of inertia, and the centroidal distance of the caving cross section. The maximum drag force exerted by a viscous drilling fluid flow passing a caving can be determined based, at least in part, on the drag coefficient, the fluid density, and the annular velocity of the drilling fluid, and the projected area of the caving body that is perpendicular to the flow direction.

If the maximum bending stress ($\sigma_B$) exceeds the caving flexural strength ($\sigma_T$) under a given stress ($\sigma_D$), the caving will break into two pieces along the surface perpendicular to the longest side L.

If the slip velocity of a caving is equal to or higher than its annular velocity, the caving will not be transported to the surface by the drilling fluid. The slip velocity is a function of caving size. As such, the maximum possible size of a spherical or subspherical caving at the surface is equal to or less than the caving size that leads to a slip velocity equal to annular velocity.

Any appropriate slip velocity model may be applied to determine the maximum caving size. For example, the slip velocity model of Equation 4 may be applied to calculate the caving slip velocity.

$$V_s = \begin{cases} 0.45\left(\dfrac{PV}{(MW)(D_p)}\right)\sqrt{\dfrac{36800}{\left(\dfrac{PV}{(MW)(D_p)}\right)^2}(D_p)\left(\dfrac{DenP}{MW}-1\right)+1}-1, & N_{Re} \le 100 \\ \\ 1.44\sqrt{D_p\left(\dfrac{DenP}{MW}-1\right)}, & N_{Re} > 100 \end{cases} \qquad \text{Equation 4}$$

In Equation 4, $V_s$ is the slip velocity in feet per minute, PV is the mud plastic viscosity in centipoise, MW is mud weight in pounds per gallon, $D_p$ is caving diameter in inches, DenP is caving density in pounds per gallon, $N_{Re}$ is the particle Reynolds number as defined by Equation 5:

$$N_{Re} = \frac{928 D_p V_s MW}{PV} \qquad \text{Equation 5}$$

If $V_s$ is equal to the annular velocity v, then the maximum caving size $d_{max}$ can be determined using Equation 6:

$$v = \begin{cases} 0.45\left(\dfrac{PV}{(MW)(D_p)}\right)\sqrt{\dfrac{36800}{\left(\dfrac{PV}{(MW)(D_p)}\right)^2}(D_p)\left(\dfrac{DenP}{MW}-1\right)+1}-1, & N_{Re} \le 100 \\ \\ 1.44\sqrt{D_p\left(\dfrac{DenP}{MW}-1\right)}, & N_{Re} > 100 \end{cases} \qquad \text{Equation 6}$$

Determining Rock Fragment Size and Size Distribution

Figure 2:
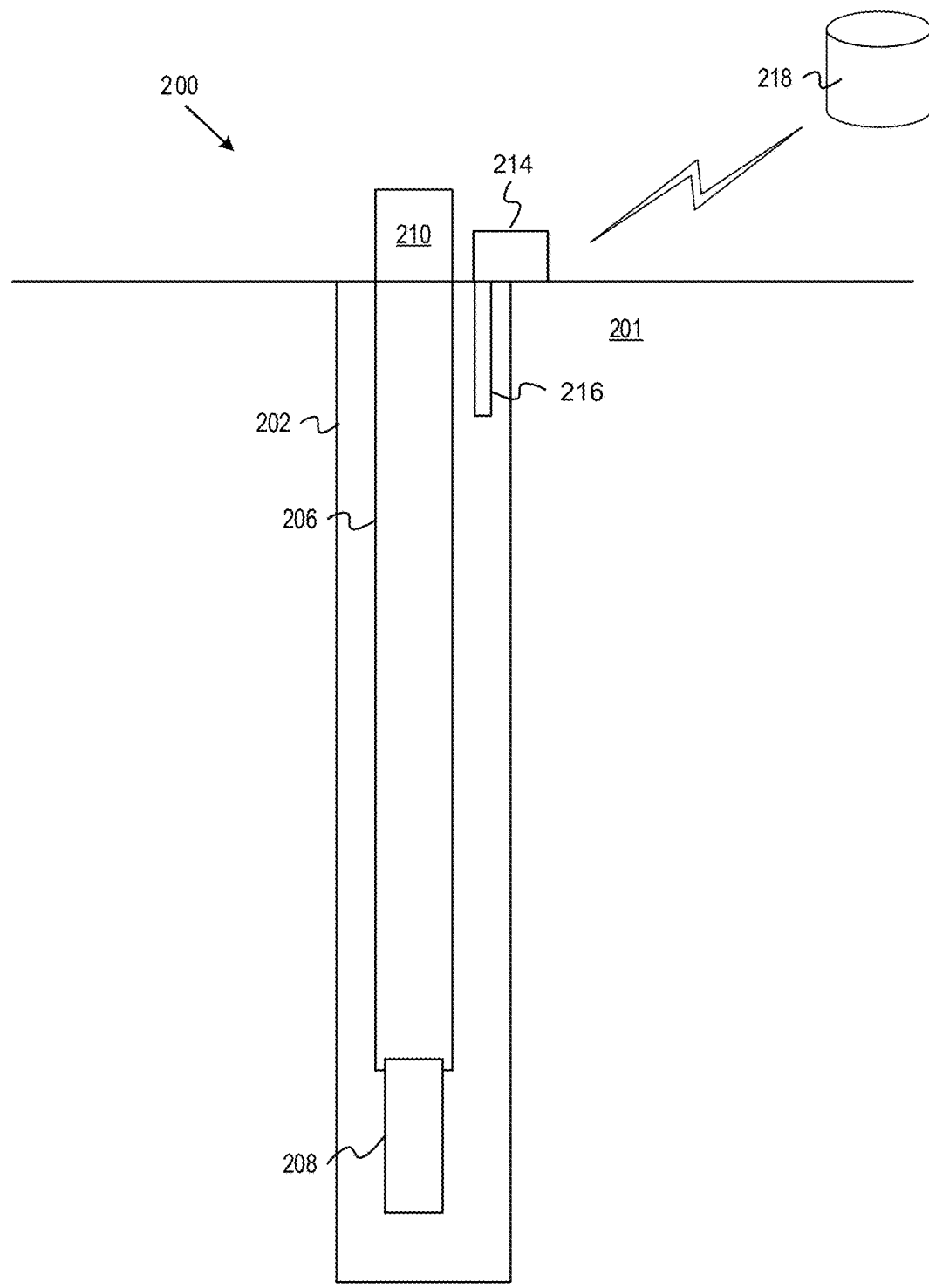
FIG. 2 depicts an example well system for which rock fragment size and size distributions may be determined, according to some implementations.

FIG. 2 depicts an example well system for which rock fragment size and size distributions may be determined, according to some implementations. In particular, FIG. 2 depicts a well system 200, including a formation 201, a wellbore 202 location in the formation 201, a tubular string 206 located in the wellbore 202, and a wellhead 210. The tubular string 206 includes a drill bit 208. The well system 200 also includes a mud return 216 and mud storage 214.

During drilling operations, drilling mud is pumped into the well system 200 via the tubular string 206 or other mechanism. The drilling mud circulates throughout the wellbore 202 and exits via the mud return 216. The mud entering the mud return 216 is sent to mud storage 214.

Analysis of the mud entering the mud return 216 generates data associated with rock fragments in the mud. The particular analysis performed may vary and may include a manual or automated sieve analysis, laser-based measurements, artificial intelligence analysis, etc. In some implementations, indirect analysis of the rock fragments might be performed. For example, analysis of the sounds generated by the rock fragments flowing within the wellbore 202 or other component of the well system 200 may be done.

The data generated by the analysis may then be persisted to the storage 218. The storage 218 may be storage of a computing system associated with the well system 200, a remote storage solution, etc.

Figure 3:
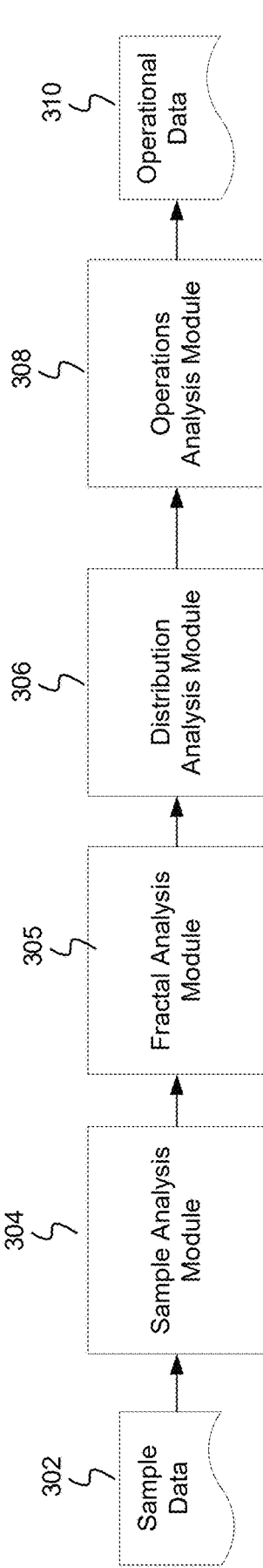
FIG. 3 depicts a system for determining rock fragment sizes and size distributions, according to some implementations.

FIG. 3 depicts a system for determining rock fragment sizes and size distributions, according to some implementations. In particular, FIG. 3 depicts a rock fragment size and size distribution analysis system 300, including a sample analysis module 304, a fractal analysis module 305, a distribution analysis module 306, and an operations analysis module 308.

In operation, the sample analysis module 304 receives sample data 302. The sample data 302 may include data for multiple samples. The specific data provided may vary depending on the implementation. For example, the sample data 302 may include data specifying the maximum size of the rock fragments in the sample, sieve sizes and, for each sieve size, a mass of rock fragments separated by the corresponding sieve. Some other examples include photographs and images of the rock fragments, laser diffraction data, and any other data usable to determine the maximum rock fragment size and the mass.

After the sample analysis module 304 receives the sample data 302, the sample analysis module 304 analyzes the sample data 302 to determine the rock fragment parameters, including the cumulative mass for each size class $$\left(\frac{M(\text{cutting size} < d)}{M_T}\right)$$

and the ratio of the maximum rock fragment size for the size class to the maximum rock fragment size $$\left(\frac{d}{d_{max}}\right).$$

The particular analysis performed by the sample analysis module 304 may vary depending on the implementation. For example, if the sample data 302 includes data specifying the maximum size of the rock fragments in the sample, sieve sizes and, for each sieve size, a mass of rock fragments separated by the corresponding sieve, the sample analysis module 304 may calculate the rock fragment parameters by using the equations specified herein. If the sample data 302 includes photographs and images of the rock fragments or laser diffraction data, the sample analysis module 304 may use artificial intelligence/machine learning or other techniques to determine the rock fragment parameters based on the photographs and images of the rock fragments. For other types of sample data 302, the implementation of the sample analysis module 304 may vary accordingly.

The sample analysis module 304 may perform multiple analyses and determine multiple sets of rock fragment parameters. For example, if cuttings and cavings may have different rock fragment parameters and thus the sample analysis module 304 may perform an analysis for each.

After the sample analysis module 304 determines the rock fragment parameters, the fractal analysis module 305 determines the fractal dimension based on the rock fragment parameters. The particular analysis performed by the fractal analysis module 305 to determine the fractal dimension can vary between implementations and can be any method usable to determine the fractal dimension or the corresponding distribution. For example, the fractal analysis module 305 may perform a linear regression using Equation 2 with the rock fragment parameters determined by the sample analysis module 304.

After the fractal analysis module 305 determines the fractal dimension, the distribution analysis module 306 determines the rock fragment distribution. The particular analysis performed by the distribution analysis module 306 can vary between implementations and can be any method usable to determine the rock fragment distribution. For example, the distribution analysis module 306 may use Equation 3 to determine the rock fragment distribution.

After the distribution analysis module 306 determines the rock fragment distribution, the operations analysis module 308 determines whether one or more operational changes should be made based on the rock fragment distribution. For example, if the rock fragment distribution shows a distribution biased towards larger rock fragments the operations analysis module 308 may generate operational data 310 indicating a particular mud weight or viscosity.

The operational data 310 can vary between implementations. For example, the operational data 310 may specify operational parameters and characteristics (e.g., mud weight, viscosity, composition, drill bit parameters, etc.), changes to operational parameters and characteristics, commands or instructions that change downhole operations, etc.

The sample data 302 may be recollected if the well system operating parameters or characteristics change. Examples of operating parameters or characteristics that might change and result in the recollection of the sample data 302 include rock properties (rock strength), drilling parameters (weight on bit, torque on bit and rotations per minute) and drill bit (type and size).

Although depicted as being implemented across separate modules, the functionality of the rock fragment size and size distribution analysis system 300 may be combined into fewer modules or split across more modules.

One or more of the modules of the rock fragment size and size distribution analysis system 300 may be implemented via one or more computing systems, including cloud-based computing systems.

Figure 4:
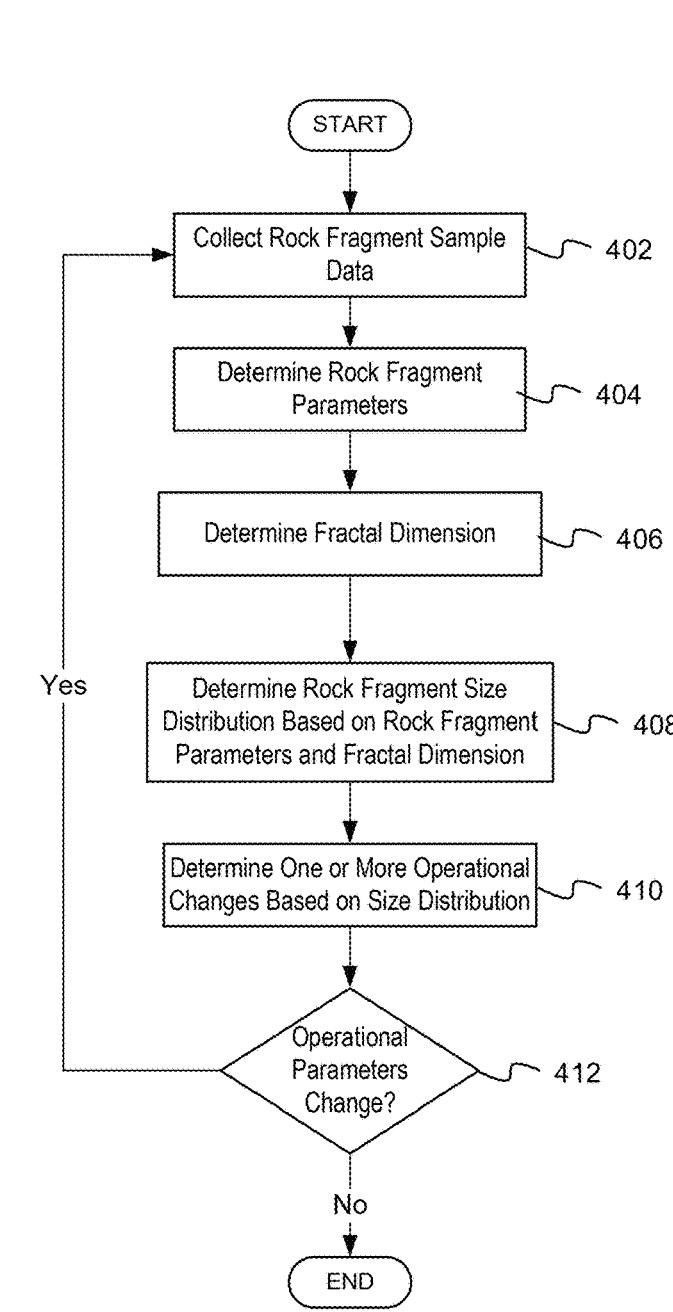
FIG. 4 is a flowchart of operations for determining rock fragment sizes and size distributions, according to some implementations.

FIG. 4 is a flowchart of operations for determining rock fragment sizes and size distributions, according to some implementations. In particular, FIG. 4 depicts a flowchart 400 of operations that begin at block 402. The operations depicted in FIG. 4 may be performed by the rock fragment size and size distribution analysis system 300 or any system capable of performing the operations.

At block 402, rock fragment sample data is collected. The rock fragment sample data may be collected manually or may be collected automatically. For example, a well system operator may manually collect a sampling of rock fragments during operation of the well system and may manually perform a sieve analysis, collecting the relevant sample data. As another example, the processing of the mud exiting the wellbore may include the application of automatic sampling techniques. As another example, some implementations may include a combination of manual and automatic sample data collection. For example, a well system operator may manually collect the samples and place them in a component that performs laser diffraction analysis.

As an example of using sieve analysis, rock fragments may be collected at the outlet of a shale shaker on a well system rig during drilling operations. The sample may conform to specific parameters, such as a specific total mass or all rock fragments collected within a certain period of time. The size of the sample may vary depending on whether the rock fragments are wet or dry and the amount that ensures a statistically representative sample.

Once the sample is collected, the sieve analysis may use different sized sieves to divide the sample into size classes. If the rock fragments are wet, the rock fragments may be dried prior to performing the sieve analysis. The sieve analysis also determines the maximum rock fragment size (i.e., $D_{max}$). The mass of the rock fragments in each size class is measured. The number of sieves used (and thus the number of size classes) may vary depending on the subsequent analyses performed on the sample data. For example, if determining the fractal dimension by performing a linear regression, three sieve sizes can be used to generate four data points for the regression. Similarly, the sieves sizes may be selected such that the sieve sizes are as uniform as possible.

At block 404, the rock fragment parameters are determined. The rock fragment parameters are determined based on the sample data collected during the previous step and may include the cumulative mass for each size class $$\left( \frac{M(\text{cutting size} < d)}{M_T} \right)$$

and the ratio of the maximum rock fragment size for the size class to the maximum rock fragment size $$\left( \frac{d}{d_{max}} \right).$$

At block 406, the fractal dimension is determined. Any analysis that is usable to determine the fractal dimension may be employed. For example, to perform a regression analysis, the data points (x, y), where $$x \text{ is } \log \frac{d}{d_{max}}$$

and $$y \text{ is } \log \frac{M(\text{cutting size} < d)}{M_T},$$

may be determined based on the analysis in the previous step. A line of best fit for the data points may be determined using the least squares method and the slope of the line may be used to determine the fractal dimension (e.g., D=3-slope).

At block 408, the rock fragment size distribution is determined based on the rock fragment parameters and the fractal dimension. Any analysis that is usable to determine the rock fragment size distribution may be used. For example, varying diameter sizes may be inserted into Equation 3 to calculate the rock fragment size distribution.

At block 410, one or more operational changes is determined based on the rock fragment size distribution. The operational changes may include changes to the drilling fluid, changes to the drilling operations, etc.

At block 412, it is determined whether operational parameters of the well system have changed. In particular, it is determined whether the operational parameters of the well system have changed in a manner that might result in a different rock fragment distribution, such as rock properties (rock strength), drilling parameters (weight on bit, torque on bit and rotations per minute) and drill bit (type and size). This may be done manually by well system operators after changes to the well system are made. It may also be done automatically by comparing the current parameters with previous parameters. As another example, well system operators may continue to collect rock fragment samples as done at 402 and may thus monitor the samples for actual changes.

If it is determined that operational parameters have changed, control flows back to block 402. If it is determined that the operational parameters have not changed, the process ends.

In some implementations, the operations at block 412 may be repeated until a trigger results in the operations ending. For example, the operations at block 412 may be performed until the drilling operations are completed.

Figure 5:
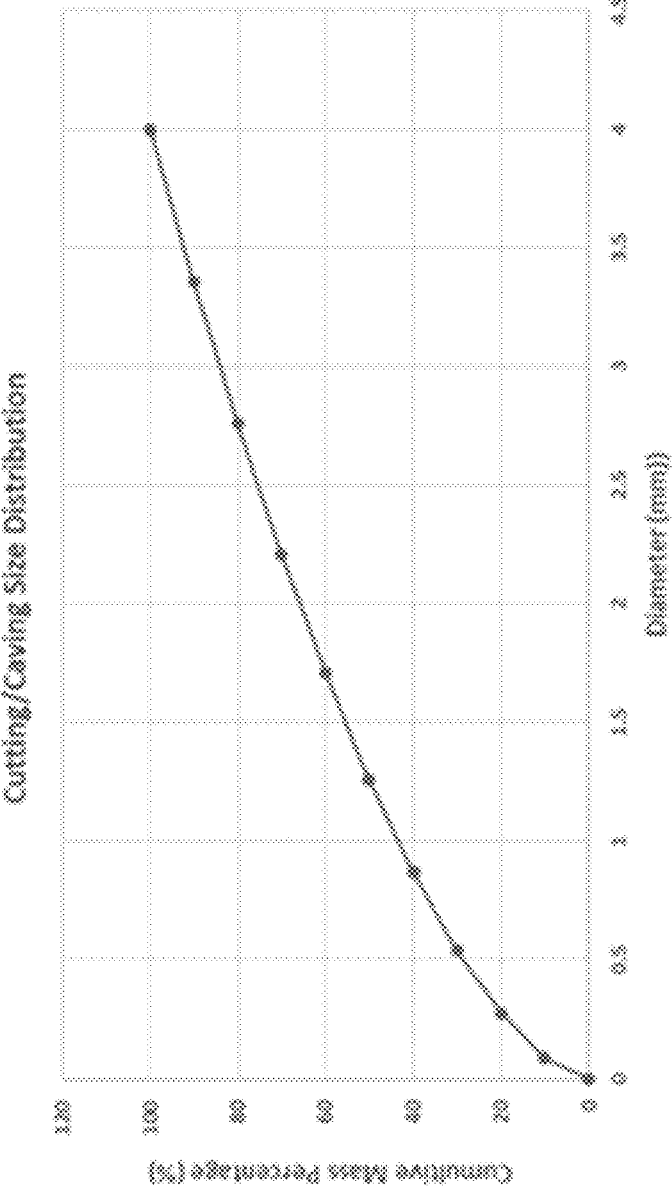
FIG. 5 depicts an example rock fragment distribution, according to some implementations.

FIG. 5 depicts an example rock fragment distribution, according to some implementations. In particular, FIG. 5 includes a graph 500 depicting an example rock fragment distribution. In this example, the distribution illustrates the relationship between the diameter of the rock fragments and the cumulative mass percentage (i.e., the total mass of the rock fragments smaller than the specified diameter).

Predicting Rock Fragment Size and Size Distribution

For well systems in the design phase or which taking samples of the rock fragments is not feasible, predicting rock fragment size and size distribution can allow well system operators to take into account the rock fragment size and size distribution.

Figure 6:
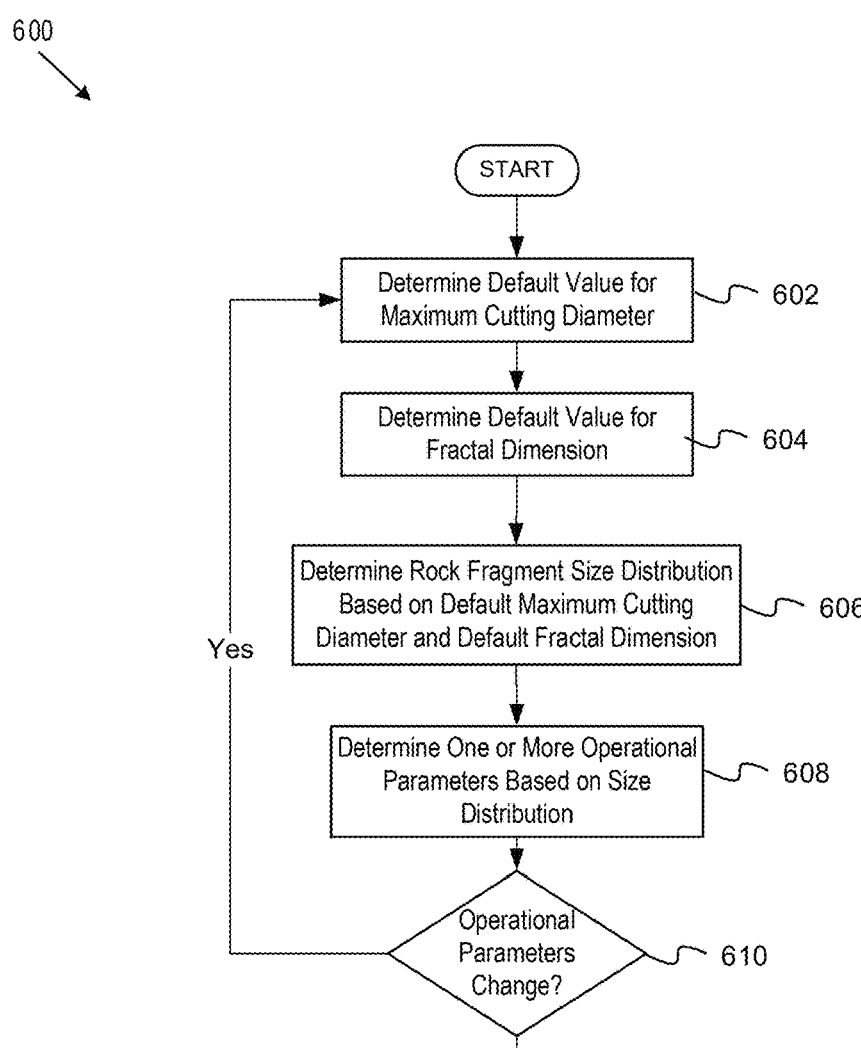
FIG. 6 is a flowchart of operations for predicting cutting sizes and size distributions, according to some implementations.

FIG. 6 is a flowchart of operations for predicting cutting sizes and size distributions, according to some implementations. In particular, FIG. 6 depicts a flowchart 600 of operations that begin at block 602. The operations depicted in FIG. 6 may be performed by the rock fragment size and size distribution analysis system 300 or any system capable of performing the operations.

At block 602, a default value for the maximum cutting diameter ($d_{max}$) is determined. The default value for the maximum cutting diameter can be determined using any appropriate technique. For example, a well system designer may select a maximum cutting diameter based on previous well systems with similar design and operational parameters. As another example, the operational parameters for the proposed well system may be provided as input to a machine learning model that has been trained on data that includes the operational parameters and cutting sizes for existing well systems. The maximum cutting diameter can be also updated by visual inspection of cuttings on shale shaker.

At block 604, a default value for the fractal dimension (D) is determined. The default value for the fractal dimension can be determined using any appropriate technique. For example, a well system designer may select a fractal dimension based on previous well systems with similar operational parameters. As another example, the operational parameters for the proposed well system may be provided as input to a machine learning model that has been trained on data that includes the operational parameters and cutting sizes for existing well systems.

At block 606, the rock fragment size distribution is determined based on the default maximum cutting diameter and the fractal dimension. Any analysis usable to determine the rock fragment size distribution may be used. For example, varying diameter sizes may be inserted into Equation 3 to calculate the rock fragment size distribution.

At block 608, one or more operational parameters is determined based on the rock fragment size distribution. The operational parameters may include the components of the drilling fluid, parameters of the drilling operations, etc.

At block 610, it is determined whether operational parameters of the well system have changed. For example, the well system design may be modified to adjust various operational parameters, such as the drilling fluid parameters, drill bit parameters, etc. If it is determined that the operational parameters of the well system have changed, control flows back to block 602. If it is determined that the operational parameters of the well system have not changed, the process ends.

In some implementations, the operations at block 610 may be repeated until a trigger results in the operations ending. For example, the operations at block 610 may be performed until the well system design is finalized.

Figure 7:
FIG. 7 is a flowchart of operations for predicting caving sizes and size distributions, according to some implementations.
Figure 7:
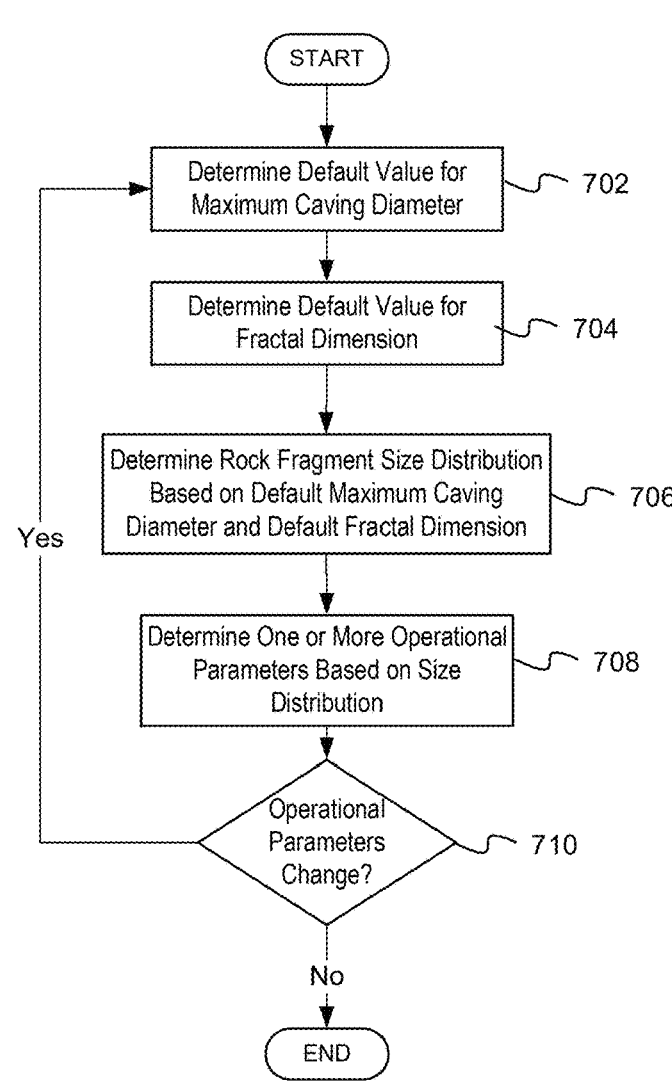

FIG. 7 is a flowchart of operations for predicting caving sizes and size distributions, according to some implementations. In particular, FIG. 7 depicts a flowchart 700 of operations that begin at block 702. The operations depicted in FIG. 7 may be performed by the rock fragment size and size distribution analysis system 300 or any system capable of performing the operations.

At block 702, a default value for the maximum caving diameter ($d_{max}$) is determined. The default value for the maximum caving diameter can be determined using any appropriate technique. For example, if the cavings are expected to be elongated, as might be the case with a highly laminated formation or massive shale formation, the maximum caving diameter may be determined based, at least in part, on the maximum bending stress of an elongated caving, the maximum drag force exerted by the drilling fluid, and the operational parameters for the proposed well system (e.g., the actual expected annular velocity and mud density). If the cavings are expected to be spherical or subspherical, as might be the case with a fractured/faulted formation, the maximum caving diameter may be determined using Equation 6 using the operational parameters for the proposed well system (e.g., the actual expected annular velocity, mud density, and plastic viscosity). Caving density may be determined based on a density log from existing offset well systems or may be set to a default parameter based on analysis of existing well systems, prior experience, etc. The maximum caving diameter can be also updated by visual inspection of cavings on shale shaker.

At block 704, a default value for the fractal dimension (D) is determined. The default value for the fractal dimension can be determined using any appropriate technique. For example, a well system designer may select a fractal dimension based on previous well systems with similar operational parameters. As another example, the operational parameters for the proposed well system may be provided as input to a machine learning model that has been trained on data that includes the operational parameters and cutting sizes for existing well systems.

At block 706, the rock fragment size distribution is determined based on the default maximum caving diameter and the fractal dimension. Any analysis usable to determine the rock fragment size distribution may be used. For example, varying diameter sizes may be inserted into Equation 3 to calculate the rock fragment size distribution.

At block 708, one or more operational parameters is determined based on the rock fragment size distribution. The operational parameters may include the components of the drilling fluid, parameters of the drilling operations, etc.

At block 710, it is determined whether operational parameters of the well system have changed. For example, the well system design may be modified to adjust various operational parameters, such as the drilling fluid parameters, drill bit parameters, etc. If it is determined that the operational parameters of the well system have changed, control flows back to block 702. If it is determined that the operational parameters of the well system have not changed, the process ends.

Figure 8:
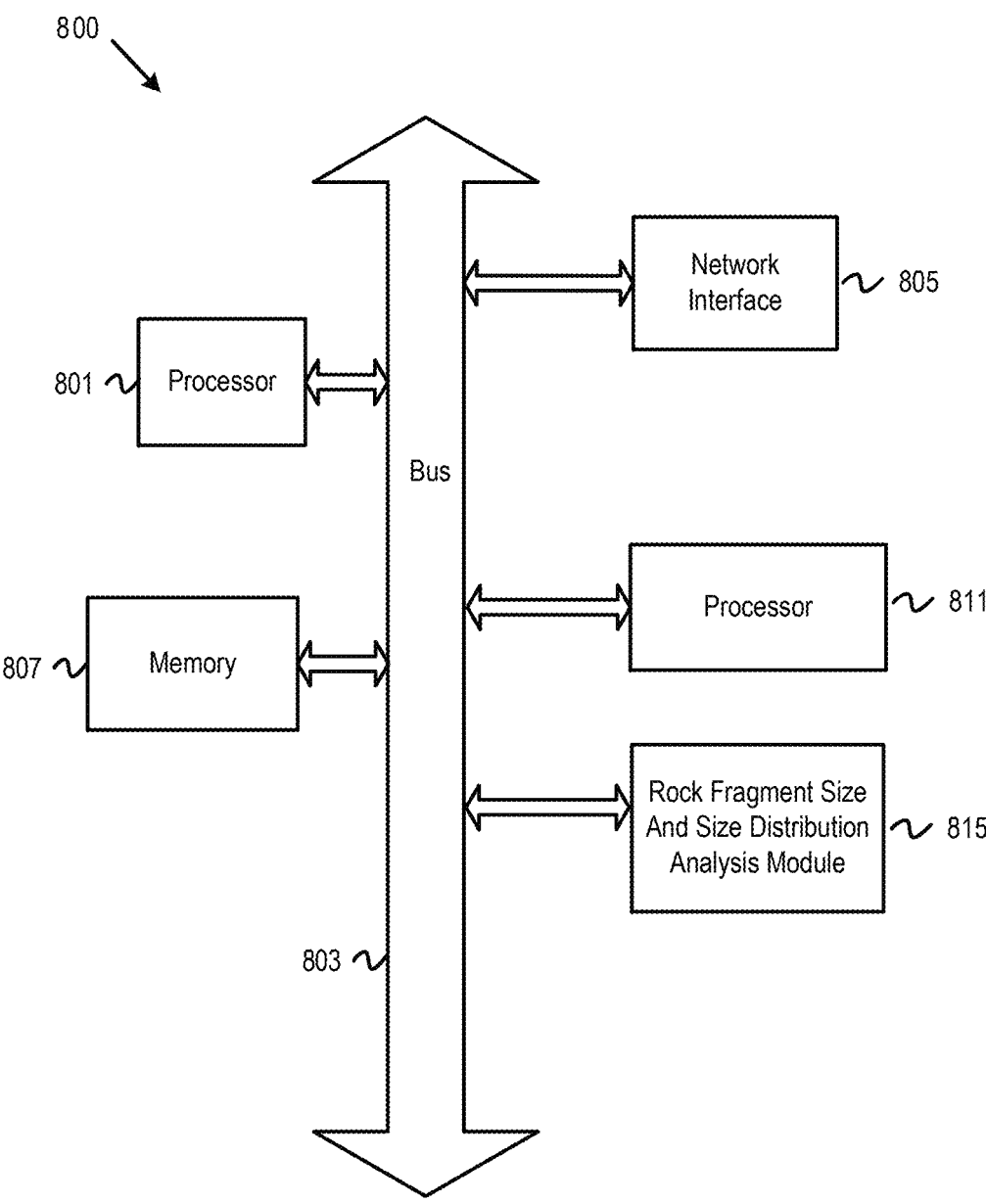
FIG. 8 is a block diagram depicting an example computing system, according to some implementations.

In some implementations, the operations at block 710 may be repeated until a trigger results in the operations ending. For example, the operations at block 710 may be performed until the well system design is finalized.
Example Computing Systems FIG. 8 is a block diagram depicting an example computing system, according to some implementations. FIG. 8 depicts a computing system 800 for determining or predicting rock fragment sizes and size distributions. The computing system 800 includes a processor 801 (possibly including multiple processors, multiple cores, multiple nodes, and/or implementing multi-threading, etc.). The computing system 800 also includes a rock fragment size and size distribution analysis module 815. The rock fragment size and size distribution analysis module 815 may perform the operations described herein. For example, the rock fragment size and size distribution analysis module 815 may analyze sample data corresponding to rock fragments from an operating well system or a well system being designed; determine rock fragment parameters (including a maximum rock fragment size and a cumulative mass for multiple size classes) based on the sample data; determine a fractal dimension based on the rock fragment parameters; determine a rock fragment distribution based on the fractal dimension; and, determine one or more operational changes or operational parameters based on the rock fragment distribution. Any one of the previously described functionalities may be partially (or entirely) implemented in hardware and/or on the rock fragment size and size distribution analysis module 815. For example, the functionality may be implemented with an application specific integrated circuit, in logic implemented in the rock fragment size and size distribution analysis module 815, in a co-processor on a peripheral device or card, etc. Further, realizations may include fewer or additional components not illustrated in FIG. 8 (e.g., video cards, audio cards, additional network interfaces, peripheral devices, etc.). The processor 801 and the network interface 805 are coupled to the bus 803. Although illustrated as being coupled to the bus 803, the memory 807 may be coupled to the processor 801. The computing system 800 includes memory 807. The memory 807 may be system memory or any one or more possible realizations of machine-readable media. The computing system 800 can communicate via transmissions to and/or from remote devices via the network interface 805 in accordance with a network protocol corresponding to the type of network interface, whether wired or wireless and depending upon the carrying medium. In addition, a communication or transmission can involve other layers of a communication protocol and or communication protocol suites (e.g., transmission control protocol, Internet Protocol, user datagram protocol, virtual private network protocols, etc.).

While the aspects of the disclosure are described with reference to various implementations and exploitations, it will be understood that these aspects are illustrative and that the scope of the claims is not limited to them. In general, techniques for determining rock fragment size distributions as described herein may be implemented with facilities consistent with any hardware system or hardware systems. Many variations, modifications, additions, and improvements are possible.

Plural instances may be provided for components, operations or structures described herein as a single instance. Further, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

The flowcharts are provided to aid in understanding the illustrations and are not to be used to limit the scope of the claims. The flowcharts depict example operations that can vary within the scope of the claims. Additional operations may be performed; fewer operations may be performed; the operations may be performed in parallel; and the operations may be performed in a different order. It will be understood that each block of the flowchart illustrations and/or block diagrams, and combinations of blocks in the flowchart illustrations and/or block diagrams, can be implemented by program code. The program code may be provided to a processor of a general-purpose computer, special purpose computer, or other programmable machine or apparatus.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

As used herein, the term "or" is inclusive unless otherwise explicitly noted. Thus, the phrase "at least one of A, B, or C" is satisfied by any element from the set $\{A, B, C\}$ or any combination thereof, including multiples of any element.

Example Implementations

Implementation 1: A method for determining a rock fragment size and size distribution, the method comprising determining rock fragment parameters associated with a well system; determining a fractal dimension based, at least in part, on the rock fragment parameters; and determining a rock fragment size distribution based, at least in part, on the fractal dimension.

Implementation 2: The method according to Implementation 1, wherein at least one of a downhole operation or a downhole attribute in a wellbore of the well system is modified based, at least in part, on the rock fragment size distribution.

Implementation 3: The method according to any of the preceding implementations, further comprising directing an operation to modify at least one of a downhole operation or a downhole attribute in a wellbore of the well system based, at least in part, on the rock fragment size distribution.

Implementation 4: The method according to any of the preceding implementations, further comprising modifying at least one of a downhole operation or a downhole attribute in a wellbore of the well system based, at least in part, on the rock fragment size distribution.

Implementation 5: The method according to any of the preceding implementations, wherein said determining the rock fragment parameters associated with the well system comprises determining the rock fragment parameters based, at least in part, on sample data, wherein the sample data is associated with rock fragments created by drilling operations of the well system.

Implementation 6: The method according to any of the preceding implementations, wherein the rock fragment parameters comprise a maximum rock fragment size and a cumulative mass of rock fragments for a plurality of size classes.

Implementation 7: The method according to any of the preceding implementations, wherein said determining the rock fragment parameters associated with the well system comprises determining the rock fragment parameters based, at least in part, on operational parameters associated with a plurality of other well systems.

Implementation 8: A system comprising a computing system, the computing system comprising one or more processors and one or more non-transitory computer-readable mediums including instructions which, when executed by the one or more processors, cause the one or more processors to execute one or more operations for determining a rock fragment distribution, the instructions including: instructions to determine rock fragment parameters associated with a well system; instructions to determine a fractal dimension based, at least in part, on the rock fragment parameters; and instructions to determine a rock fragment size distribution based, at least in part, on the fractal dimension.

Implementation 9: The system according to Implementation 8, wherein at least one of a downhole operation or a downhole attribute in a wellbore of the well system is modified based, at least in part, on the rock fragment size distribution.

Implementation 10: The system according to any of the preceding implementations, wherein the instructions further include instructions to direct an operation to modify at least one of a downhole operation or a downhole attribute in a wellbore of the well system based, at least in part, on the rock fragment size distribution.

Implementation 11: The system according to any of the preceding implementations, wherein the instructions further include instructions to modify at least one of a downhole operation or a downhole attribute based, at least in part, on the rock fragment size distribution.

Implementation 12: The system according to any of the preceding implementations, wherein the instructions to determine the rock fragment parameters associated with the well system comprise instructions to determine the rock fragment parameters based, at least in part, on sample data, wherein the sample data is associated with rock fragments created by drilling operations of the well system.

Implementation 13: The system according to any of the preceding implementations, wherein the rock fragment parameters comprise a maximum rock fragment size and a cumulative mass of rock fragments for a plurality of size classes.

Implementation 14: The system according to any of the preceding implementations, wherein the instructions to determine the rock fragment parameters associated with the well system comprise instructions to determine the rock fragment parameters based, at least in part, on operational parameters associated with a plurality of other well system.

Implementation 15: One or more non-transitory computer-readable mediums including instructions which, when executed by a processor, cause the processor to execute one or more operations for determining a rock fragment distribution, the instructions comprising: instructions to determine rock fragment parameters associated with a well system; instructions to determine a fractal dimension based, at least in part, on the rock fragment parameters; and instructions to determine a rock fragment size distribution based, at least in part, on the fractal dimension.

Implementation 16: The one or more non-transitory computer-readable mediums according to Implementation 15, wherein at least one of a downhole operation or a downhole attribute in a wellbore of the well system is modified based, at least in part, on the rock fragment size distribution.

Implementation 17: The one or more non-transitory computer-readable mediums according to any of the preceding implementations, wherein the instructions further comprise instructions to direct an operation to modify at least one of a downhole operation or a downhole attribute in a wellbore of the well system based, at least in part, on the rock fragment distribution.

Implementation 18: The one or more non-transitory computer-readable mediums according to any of the preceding implementations, wherein the instructions further include instructions to modify at least one of a downhole operation or a downhole attribute based, at least in part, on the rock fragment size distribution.

Implementation 19: The one or more non-transitory computer-readable mediums according to any of the preceding implementations, wherein the rock fragment parameters comprise a maximum rock fragment size and a cumulative mass of rock fragments for a plurality of size classes.

Implementation 20: The one or more non-transitory computer-readable mediums according to any of the preceding implementations, wherein the rock fragment parameters comprise a maximum rock fragment size and a cumulative mass of rock fragments for a plurality of size classes.

The invention claimed is:

1. A method for determining a rock fragment size and size distribution, the method comprising:
   determining rock fragment parameters associated with a well system;
   determining a fractal dimension based, at least in part, on the rock fragment parameters;
   determining a rock fragment size distribution based, at least in part, on the fractal dimension;
   determining a well system operational parameter based, at least in part, on the rock fragment size distribution; and
   modifying a downhole operation in a wellbore of the well system based, at least in part, on said determining the well system operational parameter.

2. The method of claim 1, further comprising directing an operation to modify the downhole operation in the wellbore based, at least in part, on the rock fragment size distribution.

3. The method of claim 1 wherein said determining the rock fragment parameters associated with the well system comprises determining the rock fragment parameters based, at least in part, on sample data, wherein the sample data is associated with rock fragments created by drilling operations of the well system.

4. The method of claim 1, wherein the rock fragment parameters comprise a maximum rock fragment size and a cumulative mass of rock fragments for a plurality of size classes.

5. The method of claim 1, wherein said determining the rock fragment parameters associated with the well system comprises determining the rock fragment parameters based, at least in part, on operational parameters associated with a plurality of other well systems.

6. The method of claim 1, wherein said well system operational parameter comprises at least one of drilling fluid density and viscosity.

7. The method of claim 1, wherein said downhole operation comprises pumping of drilling fluid into the wellbore.

8. The method of claim 1, wherein said modifying the downhole operation comprises modifying at least one of drilling fluid density, drilling fluid viscosity, or hydraulic pressure within the wellbore.

9. A system comprising:

a computing system comprising one or more processors and one or more non-transitory computer-readable mediums including instructions which, when executed by the one or more processors, cause the one or more processors to execute one or more operations for determining a rock fragment distribution, the instructions including:

instructions to determine rock fragment parameters associated with a well system;

instructions to determine a fractal dimension based, at least in part, on the rock fragment parameters;

instructions to determine a rock fragment size distribution based, at least in part, on the fractal dimension;

instructions to determine a well system operational parameter based, at least in part, on the rock fragment size distribution; and instructions to modify a downhole operation in a wellbore of the well system based, at least in part, on a determination of the well system operational parameter.

10. The system of claim 9, wherein the instructions further include instructions to direct an operation to modify the downhole operation in the wellbore based, at least in part, on the rock fragment size distribution.

11. The system of claim 9, wherein the instructions to determine the rock fragment parameters associated with the well system comprise instructions to determine the rock fragment parameters based, at least in part, on sample data, wherein the sample data is associated with rock fragments created by drilling operations of the well system.

12. The system of claim 9, wherein the rock fragment parameters comprise a maximum rock fragment size and a cumulative mass of rock fragments for a plurality of size classes.

13. The system of claim 9, wherein the instructions to determine the rock fragment parameters associated with the well system comprise instructions to determine the rock fragment parameters based, at least in part, on operational parameters associated with a plurality of other well systems.

14. The system of claim 9, wherein said well system operational parameter comprises at least one of drilling fluid density and viscosity.

15. The system of claim 9, wherein said downhole operation comprises pumping of drilling fluid into the wellbore.

16. The system of claim 9, wherein said instructions to modify the downhole operation comprises instructions to modify at least one of drilling fluid density, drilling fluid viscosity, or hydraulic pressure within the wellbore.

17. One or more non-transitory computer-readable mediums including instructions which, when executed by a processor, cause the processor to execute one or more operations for determining a rock fragment distribution, the instructions comprising:

instructions to determine rock fragment parameters associated with a well system;

instructions to determine a fractal dimension based, at least in part, on the rock fragment parameters;

instructions to determine a rock fragment size distribution based, at least in part, on the fractal dimension;

instructions to determine a well system operational parameter based, at least in part, on the rock fragment size distribution; and instructions to modify a downhole operation in a wellbore of the well system based, at least in part, on a determination of the well system operational parameter.

18. The one or more non-transitory computer-readable mediums of claim 17, wherein the instructions further comprise instructions to direct an operation to modify the downhole operation in the wellbore based, at least in part, on the rock fragment distribution.

19. The one or more non-transitory computer-readable mediums of claim 17, wherein the rock fragment parameters comprise a maximum rock fragment size and a cumulative mass of rock fragments for a plurality of size classes.

20. The one or more non-transitory computer-readable mediums of claim 17, wherein the instructions to determine the rock fragment parameters associated with the well system comprise instructions to determine the rock fragment parameters based, at least in part, on operational parameters associated with a plurality of other well systems.

21. The one or more non-transitory computer-readable mediums of claim 17, wherein said well system operational parameter comprises at least one of drilling fluid density and viscosity.

22. The one or more non-transitory computer-readable mediums of claim 17, wherein said downhole operation comprises pumping of drilling fluid into the wellbore.

23. The one or more non-transitory computer-readable mediums of claim 17, wherein said instructions to modify the downhole operation comprises instructions to modify at least one of drilling fluid density, drilling fluid viscosity, or hydraulic pressure within the wellbore.

\* \* \* \* \*